United States Patent [19]

Pennington, Sr.

[11] Patent Number: Plant 7,702

[45] Date of Patent: Nov. 5, 1991

[54] *PENTAS LANCEOLATA* PLANT NAMED JESSICA

[76] Inventor: Russell R. Pennington, Sr., 10500 Isabelle Rd., Lafayette, Colo. 80026

[21] Appl. No.: 517,080

[22] Filed: May 1, 1990

[51] Int. Cl.[5] ..... A01H 5/00

[52] U.S. Cl. ..... Plt./68

[58] Field of Search ..... Plt./68

[56] References Cited

PUBLICATIONS

Bailey, L. H., "Pentas", *The Standard Cyclopedia of Horticulture,* vol. III, The MacMillan Co., New York (1935) (spanning), pp. 2538–2539.

*Primary Examiner*—James R. Feyrer

*Attorney, Agent, or Firm*—Foley & Lardner

[57] ABSTRACT

A *Pentas lanceolata* plant named Jessica, having the combined characteristics of bright red-purple flower color, vigorous growth, relatively long ovate to lanceolate shaped leaves, and by its continuous flowering.

1 Drawing Sheet

1

The present invention relates to a new and distinctive cultivar of *Pentas lanceolata,* referred to by the cultivar name Jessica. The species is also referred to by the common name Egyptian Star-Cluster.

*Pentas lanceolata* are herbs or shrubs of the Rubiaceae family, and are native to Africa and Madagascar. They can be cultivated in greenhouses on a year-round basis, and can also serve as bedding plants in the southern part of the United States.

The new cultivar Jessica is a sport or mutation and was discovered in July 1989 in Lafayette, Col. by the inventor Russell R. Pennington, Sr. while growing among a group of stock plants of the parent *Pentas lanceolata* cultivar named Ruby Glow Red. The parent cultivar can be generally described as being up to approximately 30" in height, 24–28" in width, having ovate to lanceolate leaves of up to approximately 3.5", and by its fully open flower color of approximately 45B, as measured by The Royal Horticultural Society Colour Chart. The flower color is a very vivid and bright red. The new cultivar Jessica was noted by virtue of its fuschia or bright red-purple flower color.

Asexual reproduction of Jessica by the inventor by cuttings has demonstrated that the unique features of the new cultivar are stabilized and are reproduced true to type in successive propagations.

Jessica is similar in many respects to the parent cultivar Ruby Glow Red. However, it is distinguished from its parent by its flower color as above described, its more vigorous growth habit, and its somewhat longer and more pubescent leaves.

The following characteristics in combination distinguish the new cultivar Jessica from its parent and from other cultivars of the same general type:

1. Bright red-purple flower color.
2. Vigorous growth habit, reaching 36" in height and approximately 34–36" in width when fully grown.
3. Its relatively large leaves, which are ovate to lanceolate in shape, and up to 4½" long.
4. Continuous flowering.

The accompanying colored photograph illustrates a plant of the new cultivar in front perspective view, with the photograph showing flower and leaf color as true as it is reasonably possible to obtain in a colored reproduction of this type. The photograph is of a single plant six months old grown in a 16" pot.

2

The following is a detailed description of my new cultivar Jessica based on plants grown in a typical commercial environment in greenhouse facilities at Lafayette, Col. Color references are made to The Royal Horticultural Society Colour Chart except where general terms of ordinary dictionary significance are used.

Classification:

*Botanical.*—*Pentas lanceolata* cv Jessica.

*Commercial.*'3 Egyptian Star-Cluster.

Parentage: Sport or mutation of *Pentas lanceolata* Ruby Glow Red.

Propagation: Vegetatively by meristem; rooting habit excellent.

PLANT DESCRIPTION

A. Form: Generally round.

B. Habit of growth: Very vigorous; plants can reach 36" in height and 34–36" in diameter.

*Average water requirements.*—Approximately one inch per week is adequate in outdoor full sun conditions in summer.

C. Foliage:

1. *Size.*—Approximately 4–4.5" in length when fully mature.
2. *Shape.*—Ovate to lanceolate, oppositely arranged, stipules divided.
3. *Texture.*—Pubescent.
4. *Margin.*—Smooth.
5. *Color.*—Young foliage, top side 137D at base to 137A-B at tip; under side 137D. Mature foliage, top side between 137A and 136B; under side 137D.
6. *Venation.*—138B-C.

FLOWERING DESCRIPTION

A. Flowering habits: Flowering is in terminal corymbs.

B. Natural flowering season: Continuous flowering in greenhouse environment.

C. Flower bud description: Calyx lobes unequal, lanceolate to linear, and ⅛" to ¼" long.

D. Flowers borne: In terminal corymbs; corolla tube ½" to ¾" long.

E. Quantity of flowers: Numerous; no pinching required for continued blooming.

F. Petals:

1. *Shape.*—Star-shaped; five petals, 5–6 mm. in length and approximately 3 mm. in width (at widest point).
2. *Color.*—Top side when just opening 57A, turning to 57B when fully open; maintains color with very little fading.

3. *Size of flowers.*—Corolla $\frac{3}{8}''$ to $\frac{1}{2}''$ in diameter.

G. Reproductive organs: Normal.

Disease resistance: No disease problems noted to date.

Fragrance: None.

Seed production: Seed is formed but is not viable.

I claim:

1. A new and distinct cultivar of *Pentas lanceolata* plant named Jessica, as illustrated and described.

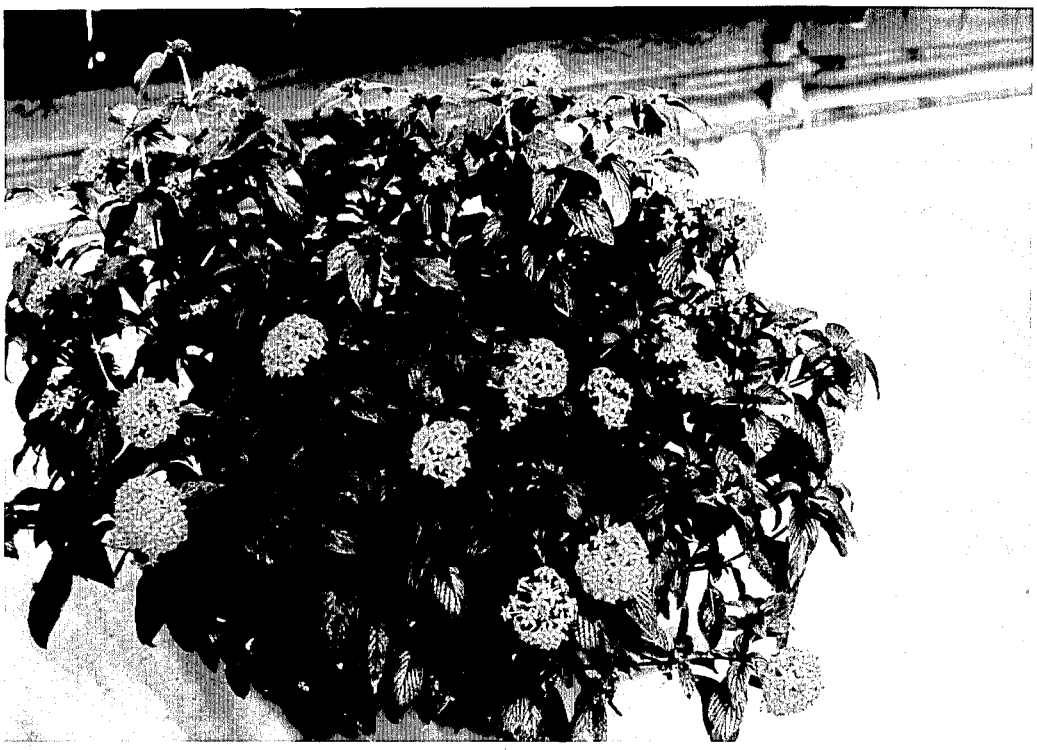

* * * * *